United States Patent
Luce

(10) Patent No.: US 6,875,175 B2
(45) Date of Patent: Apr. 5, 2005

(54) DUEL MODE NON-CONTACT TONOMETER

(75) Inventor: David A. Luce, Clarence Center, NY (US)

(73) Assignee: Reichert, Inc., Depew, NY (US)

(*) Notice: Subject to any disclaimer, the term of this patent is extended or adjusted under 35 U.S.C. 154(b) by 64 days.

(21) Appl. No.: 10/186,572

(22) Filed: Jul. 1, 2002

(65) Prior Publication Data

US 2004/0002639 A1 Jan. 1, 2004

(51) Int. Cl.[7] .............................................. A61B 3/16
(52) U.S. Cl. ................................................. 600/398
(58) Field of Search .............................. 600/398, 401, 600/405, 399, 561, 587; 351/205, 208

(56) References Cited

U.S. PATENT DOCUMENTS

| | | | |
|---|---|---|---|
| 5,279,300 A | * | 1/1994 | Miwa et al. ................. 600/401 |
| 5,474,066 A | | 12/1995 | Grolman |
| 6,159,148 A | | 12/2000 | Luce |
| 6,419,631 B1 | | 7/2002 | Luce |
| 6,616,609 B2 | * | 9/2003 | Siskowski et al. .......... 600/401 |

* cited by examiner

Primary Examiner—Eric F. Winakur
Assistant Examiner—Brian Szmal
(74) Attorney, Agent, or Firm—Hodgson Russ LLP

(57) ABSTRACT

A dual mode non-contact tonometer allows selection between a standard measurement mode for patient comfort and an alternate measurement mode wherein pressure-time characteristics of the fluid pulse are varied to allow additional observation of corneal hysteresis associated with the dynamic measurement process. In the alternate measurement mode, measured intraocular pressure corresponding to inward applanation of the cornea and corneal hysteresis derived from a pressure differential associated with inward and outward applanation events in the same measurement pulse allows comparison with a predetermined population normality function to avoid corneal effects so that the actual status of intraocular pressure can be ascertained.

8 Claims, 6 Drawing Sheets

DUEL MODE NON-CONTACT TONOMETER

FIELD OF THE INVENTION

The present invention relates generally to the field of ophthalmic instruments, and particularly to a dual mode non-contact tonometer capable of operation in different measurement modes having distinct fluid pulse characteristics.

BACKGROUND OF THE INVENTION

Tonometers for measuring IOP (intraocular pressure) were originally developed as "contact" type instruments, meaning that a portion of the instrument is brought into contact with the cornea during the measurement procedure. A well-known instrument of this type is the Goldmann applanation tonometer originally developed during the 1950s. The GAT measures the force required to flatten ("applanate") a known area of the cornea, and is used today as a standard against which other types of tonometers are calibrated and compared to assess measurement accuracy.

Patient discomfort and the requirement to use anesthesia related to contact tonometers such as the GAT led to the development of "non-contact" tonometers (NCTs) which operate by directing an air pulse at the cornea to cause applanation. Typically, the air pulse is generated by a solenoid driven pump mechanism and directed through a narrow fluid discharge tube at the cornea. As the cornea is deformed by the fluid pulse, an opto-electronic system monitors the cornea by detecting corneally reflected light from a beam incident upon the cornea, and a peak detector signal occurs at the moment of applanation when the reflecting surface of the cornea is flat.

In state of the art NCTs, a pressure transducer detects a plenum pressure in the pump mechanism as the pulse is generated and provides a plenum pressure signal proportional to the plenum pressure. The plenum pressure signal and applanation signal are processed to determine the plenum pressure at the moment of applanation. The plenum pressure at applanation is converted to an IOP value in units of mmHg (millimeters mercury) using a regression equation developed and stored in instrument memory during clinical calibration relative to GAT as a reference. A primary index of an NCT's reliability is the standard deviation of differences $S_d$ of matched pairs of NCT and GAT clinical readings.

While NCTs provide reasonably reliable IOP measurements, IOP readings are occasionally falsely inflated because some of the air pulse energy is expended "bending" the corneal tissue itself, as opposed to displacing intraocular fluid pressing on the cornea. Intuitively, a cornea that is very rigid is more likely to cause a falsely elevated pressure reading because more air pulse energy is required to achieve applanation. In fact, several recent studies indicate that physical properties of the cornea can have a significant impact on NCT readings. See, for example, Copt R-P, Tomas R, Mermoud A, *Corneal Thickness in Ocular Hypertension, Primary Open-Angle Glaucoma, and Normal Tension Glaucoma, Arch Ophthalmol.* Vol. 117:14–16 (1999); Emara B, Probst L E, Tingey D P, Kennedy D W, et al., *Correlation of Intraocular Pressure and Central Corneal Thickness in Normal Myopic Eyes After Laser in situ Keratomileusis*; J Cataract Refract Surg, Vol. 24:1320–25 (1998); Stodtmeister R, *Application Tonometry and Correction According to Corneal Thickness, Acta Ophthalmol Scand*, Vol. 76:319–24 (1998); and Argus W A, *Ocular Hypertension and Central Corneal Thickness, Ophthalmol*, Vol. 102:1810–12 (1995). For persons with relatively thick corneas, IOP values measured under prior art methodology can differ significantly from "true" IOP. Heretofore, attempts to correct measured IOP for corneal thickness effects have typically involved measuring corneal thickness by additional instrument means and correcting measured IOP by an amount based upon the measured corneal thickness. U.S. Pat. No. 5,474,066 issued Dec. 12, 1995 to Grolman ascribes to this approach.

A weakness with respect to corrections based on corneal thickness is that corneal thickness is a static parameter that may or may not be a reliable indicator of a cornea's rigidity in response to dynamic loading by an air pulse or other means of applying force to cause applanation. Stated differently, corneas having the same thickness may exhibit different rigidity responses under static or dynamic loading due to differences in the corneal tissue itself. The present applicant, in his U.S. patent application Ser. No. 09/553,111, now U.S. Pat. No. 6,419,631, describes a non-contact tonometry method wherein two plenum pressures are taken into account for correlation to IOP, the first corresponding to an applanation state of the cornea upon inward deformation by an air pulse and the second corresponding to an applanation state of the cornea as it returns from a brief concave state to its normal convex state. In accordance with the described method, it is assumed that corneal rigidity force components associated with inward and outward deformation essentially cancel each other out, and the IOP measurement value is taken either by correlating the inward and outward plenum pressures to IOP based on two separate regression equations and averaging the resultant pair of IOP values, or by averaging the inward and outward plenum pressures and correlating the average pressure to IOP using a single regression equation. While this method is an improvement over the prior art, it is based on an observance of the second applanation event, which is an accidental by-product of excess impulse energy being delivered to the eye beyond the threshold level necessary to achieve the first applanation event. This excess energy is largely considered undesirable by those skilled in the art because it causes patient discomfort during testing. Consequently, developers of non-contact tonometers have sought to minimize excess impulse energy, for example by shutting off or reversing the pump driver at or before the first applanation event, building a pressure release valve or the like into the pump system, and by altering the shape of the pressure ramp itself. In this regard, please see U.S. Pat. Nos. 5,779,633; 5,165,408; and 6,159,148.

Thus, the in/out tonometry method described above suffers in certain respects. The method itself relies on dissipation of the fluid pulse in an uncontrolled manner, such that the plenum pressure as a function of time forms an asymmetrical curve about a peak pressure associated with the pump compression stroke. This fact to some extent undermines the basic assumption of force cancellation in the dynamic system. Also, the use of a non-contact tonometry method that requires delivery of excess impulse energy to the eye is largely incompatible with non-contact tonometers designed to reduce air puff discomfort felt by the patient, and may be unnecessary in situations where the patient's IOP is well within a normal range.

SUMMARY OF THE INVENTION

Therefore, it is an object of the present invention to provide a non-contact tonometer with at least two modes, one mode for taking measurements with an emphasis on minimizing impulse energy of the fluid pulse, and another mode for taking measurements with an emphasis on accounting for corneal rigidity effects to provide a measurement that gives the ophthalmic practitioner improved information regarding whether the patient's true IOP is abnormally high or low.

The invention is preferably embodied in a non-contact tonometer of a general type comprising a fluid pump system, a fluid discharge tube in communication with the fluid pump system for directing a fluid pulse at a patient's eye to cause applanation of the cornea, applanation detection means for monitoring the cornea to detect applanation caused by the fluid pulse, means for determining a fluid pressure within a plenum chamber of the fluid pump system at a moment when the cornea reaches applanation, and processing means for correlating the plenum pressure with an intraocular pressure of the patient's eye. In accordance with a preferred embodiment of the present invention, the non-contact tonometer is provided with two measurement modes characterized by different current versus time behavior for the drive current supplied to a proportional solenoid of the fluid pump system, resulting in different plenum pressure versus time behavior and different action by the fluid pulse in the two modes.

In a standard measurement mode, the solenoid drive current increases linearly with time until corneal applanation is detected, at which time the drive current is shut off. This provides a non-linear pressure ramp up to applanation for patient comfort. The plenum pressure at applanation is correlated to IOP in a well-known manner.

In an alternate measurement mode, the solenoid drive current increases linearly with time until the cornea has been deformed through a first state of applanation to a state of concavity, and then the drive current decreases linearly with time at the same rate as it increased. While the alternate measurement mode is less comfortable for the patient than the standard measurement mode, it allows for observation of plenum pressure at a first or inward applanation event (as in the standard mode) and at a second or outward applanation event occurring as the cornea returns from its concave state back toward its normal convex state. A measurement data point comprising an IOP value based on the plenum pressure at inward applanation and a hysteresis value calculated as a difference in IOP values based on the respective plenum pressures at inward and outward applanation. The alternate measurement mode provides a two-dimensional tonometric measurement wherein the first dimension depends on the force necessary to applanate the cornea and the second dimension depends on physical properties of the cornea. For evaluation purposes, the two-dimensional measurement data point is compared with a normal functional relationship between the measured IOP and hysteresis quantities to determine the degree of difference of measured IOP from normality. For example, an "excess ocular pressure" (EOP) can be reported. The normal functional relationship is predetermined during instrument calibration by fitting to clinical trial data taken with respect to a statistically large population of eyes, and is stored in instrument memory.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
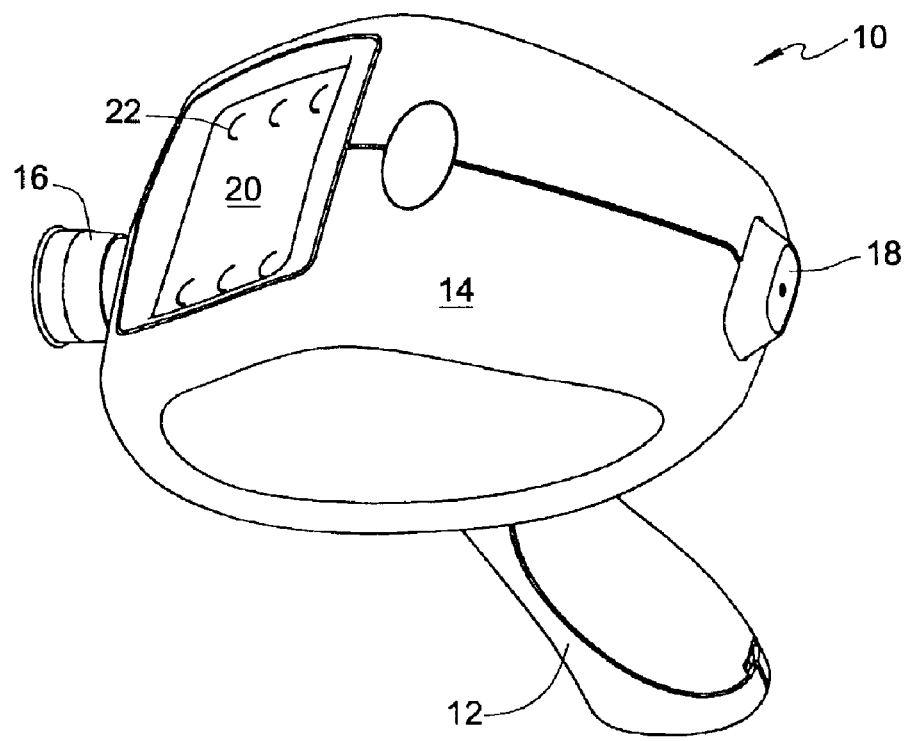
FIG. 1 is a perspective view of a non-contact tonometer embodying the present invention.

FIG. 1 of the drawings shows a handheld non-contact tonometer (NCT) 10 embodying the present invention. While the apparatus of the present invention is described in the context of a handheld NCT, it can also be embodied in a table-top NCT. NCT 10 includes a handle portion 12 and a head portion 14 at the top of the handle portion. Handle portion 12 houses a rechargeable power source for energizing alignment and tonometric measurement systems carried by head portion 14. Also visible in FIG. 1 is an operator eyepiece 16 at one end of head portion 14, a front window 18 at an opposite end of head portion 14 for facing a patient, and a liquid crystal display 20 with pushbutton control overlay 22 angled toward the operator near operator eyepiece 16.

Figure 2:
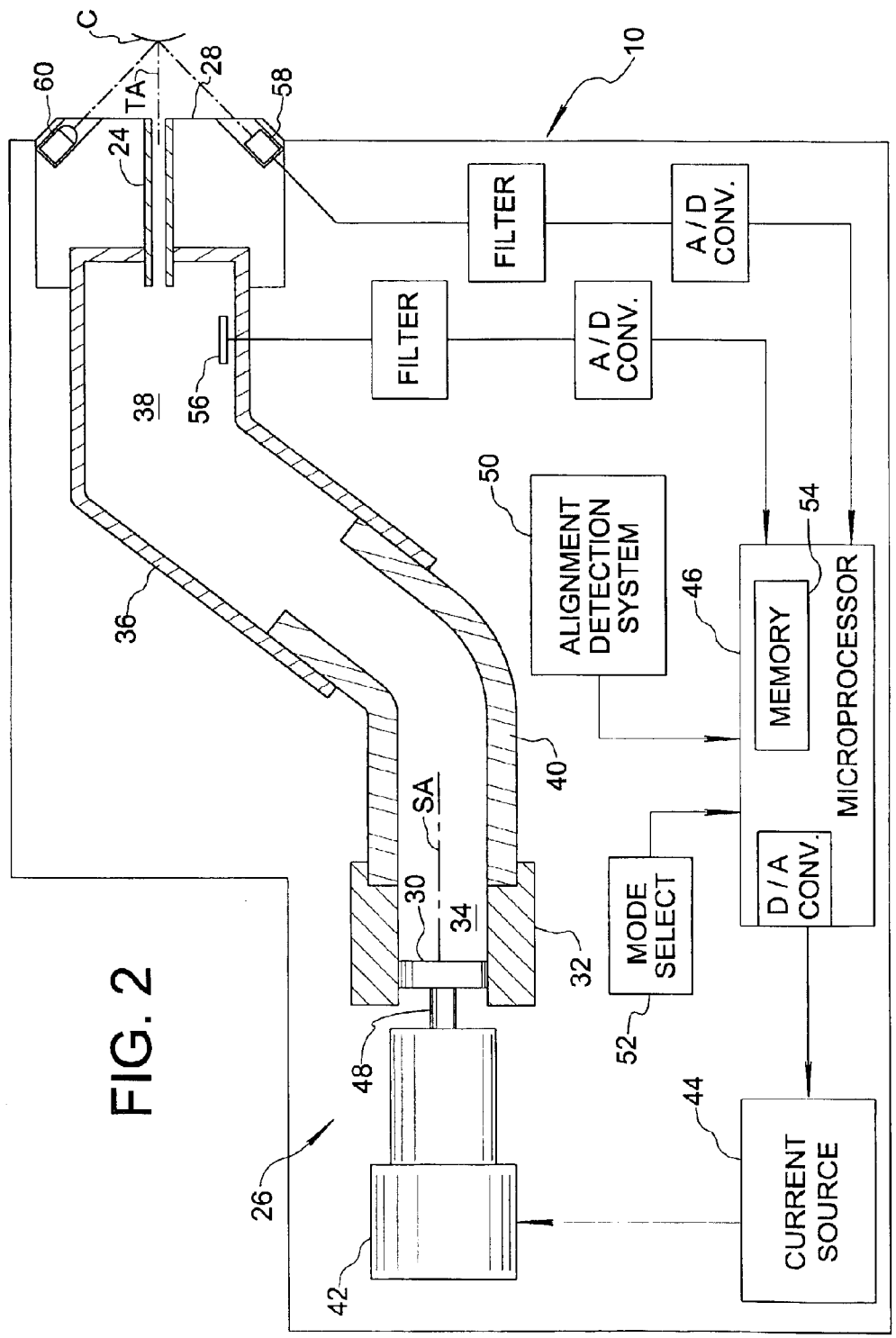
FIG. 2 is a schematic block diagram of the non-contact tonometer shown in FIG. 1.

FIG. 2 provides a schematic representation of the alignment and tonometric measurement systems housed by head portion 14. NCT 10 is operable to discharge a fluid pulse through a fluid discharge tube 24 aligned along a test axis TA to cause observable deformation of a patient's cornea C for purposes of measuring intraocular pressure. The fluid pulse is generated by a fluid pump system 26 communicating with fluid discharge tube 24, which extends through a nosepiece 28. Fluid pump system 26 preferably comprises a piston 30 axially movable relative to a cylinder 32 along a stroke axis SA for compressing fluid within an internal compression chamber 34 defined thereby, a housing 36 defining an internal plenum chamber 38, and a flow tube 40 providing a fluid conduit from compression chamber 34 to plenum chamber 38. Fluid discharge tube 24 is mounted through the wall of housing 36 for guiding pressurized fluid from plenum chamber 38 along test axis TA directed at patient cornea C.

A linear proportional solenoid 42 is operatively connected to piston 30 for causing axially directed movement of piston 30 relative to cylinder 32. A linear proportional solenoid is preferred because it is a specialized type of linear motor wherein the output driving force is proportional to the energizing current, and is most often used in connection with control valves. However, the general dual mode approach of the present invention is not intended to be limited to this particular drive means, as other drive means such as rotary solenoids may possibly be used. Proportional solenoid 42 is connected to a current source 44 which supplies energizing current to the proportional solenoid under the control of a microprocessor 46. A suitable linear proportional solenoid is a LEDEX® Linear Shift Solenoid Part No. 197887-001. As can be seen in FIG. 2, piston 30 is fixed for travel with a plunger 48 of proportional solenoid 42, as by threaded attachment or by fitted attachment with or without mechanical fasteners or adhesives.

Linear proportional solenoid 42 remains de-energized and piston 30 remains at rest until proper positioning of discharge tube 24 relative to cornea C is achieved as determined by an alignment detection system 50 connected to microprocessor 46. Alignment detection system 50 can be any suitable system, for example an alignment system as taught in commonly owned U.S. Pat. Nos. 4,881,807 and 6,361,495. Once alignment is achieved, microprocessor 46 provides a signal used by current source 44 to provide the driving current according to one of a plurality of preprogrammed ramp forms, as will now be described below.

Figure 3:
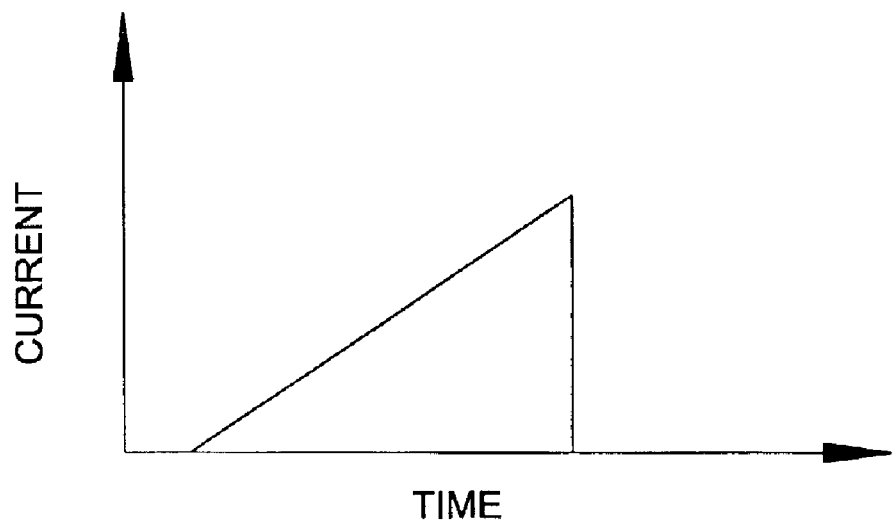
FIG. 3 is a graph of solenoid energizing current versus time in a standard operational mode of the non-contact tonometer.
Figure 5:
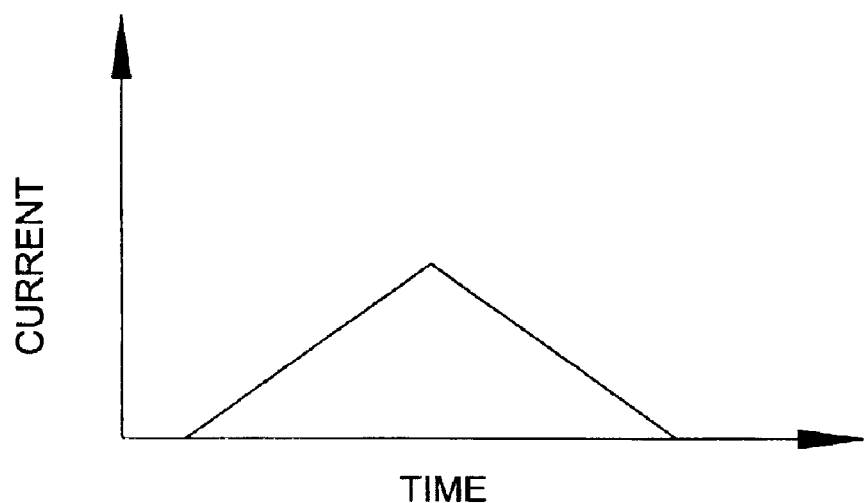
FIG. 5 is a graph of solenoid energizing current versus time in an alternate operational mode of the non-contact tonometer.

In accordance with the present invention, a measurement mode control function is part of a preprogrammed menu of functions available to the operator via liquid crystal display 20 and pushbutton control overlay 22, and is represented schematically in FIG. 2 by mode select block 52. The measurement mode control function allows the operator to choose between a plurality of different measurement modes each characterized by a different behavior of the energizing current as a function of time. More specifically, a lookup table stored in a programmable memory 54 associated with microprocessor 46 includes digital information describing a predetermined unique current versus time relationship for each respective measurement mode, which information is used to actually generate the energizing current corresponding to a selected measurement mode. By way of example, FIG. 3 depicts a current ramp corresponding to a "standard" measurement mode, while FIG. 5 depicts a current ramp corresponding to an "alternate" measurement mode.

Figure 4:
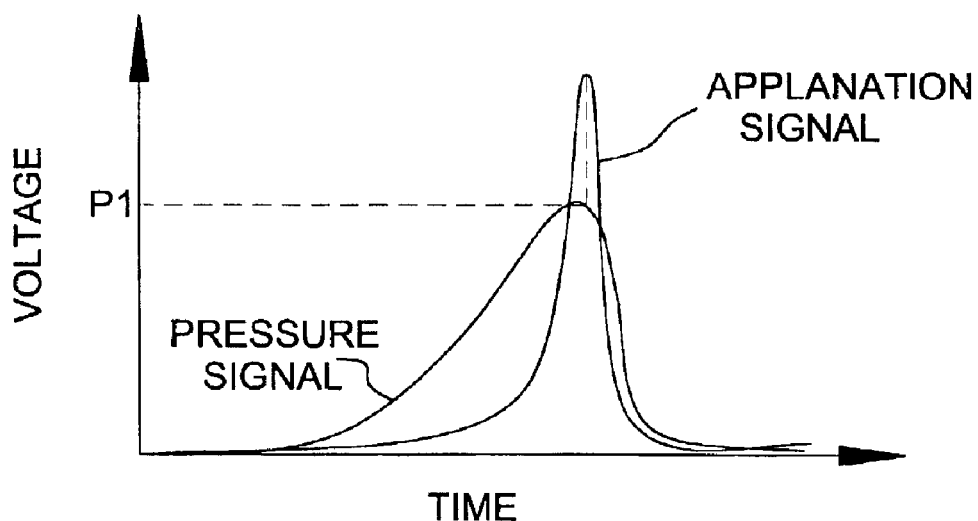
FIG. 4 is a graph of a plenum pressure signal versus time and an applanation detection signal versus time for a typical measurement stoke under the first operational mode.

The shape of the current ramp used to drive proportional solenoid 42 directly effects how the pressure within plenum chamber 38 changes as a function of time. A pressure sensor 56, for example a pressure transducer or the like, is located within plenum chamber 38 for generating a pressure signal indicative of the fluid pressure within the plenum chamber. FIG. 4 includes a plot of a pressure signal corresponding to the standard mode current ramp shown in FIG. 3. Under the standard measurement mode, measured IOP is based on correlation to the pressure within plenum chamber 38 at the moment a predetermined area of the cornea is applanated as the cornea is pushed inward from its normal convex state by the fluid pulse. In order to provide a signal indicative of the occurrence of applanation, a photosensitive detector 58 is positioned in a symmetrically oblique arrangement about test axis TA to receive corneally reflected light from emitter 60, whereby a peak signal is produced by detector 58 when the corneal surface is substantially flat for coherent reflection. Thus, the peak in the applanation signal shown in FIG. 4 represents applanation. The standard measurement mode current ramp shown in FIG. 3 increases linearly as a function of time until applanation is detected, at which time the drive current is abruptly shut off to minimize the delivery of unnecessary excess impulse energy to the eye which the patient finds uncomfortable. The ramp form shown in FIG. 3 is preferred for its simplicity and because it results in a non-linear pressure-time curve as seen in FIG. 4. As explained in commonly owned U.S. Pat. No. 6,159,148 entitled "Non-Contact Tonometer Having Non-Linear Pressure Ramp", a linearly increasing drive current produces a non-linear pressure ramp that reduces the total impulse energy delivered to the eye as compared with a constant energizing current, thereby contributing to patient comfort. Thus, in standard measurement mode, the purpose of the corresponding current ramp form is to achieve applanation while minimizing excess puff felt by the patient. Although a linearly increasing drive current is preferred for the standard mode of the present invention, other forms including a constant current may be used. IOP in the standard mode is determined according to known procedure. More specifically, the analog signal information from pressure sensor 56 and applanation detector 58 is filtered and converted to digital form for processing by microprocessor 46. The plenum pressure P1 at the time of applanation is then correlated by microprocessor 46 to an IOP value in units of mmHg (millimeters mercury) using a regression equation developed and stored in instrument memory 54 during clinical calibration relative to GAT as a reference. IOP measurement data are reported to the operator by liquid crystal display 20, and can be transmitted, preferably by wireless transmission, to a printing device and/or a remote computer.

Figure 6:
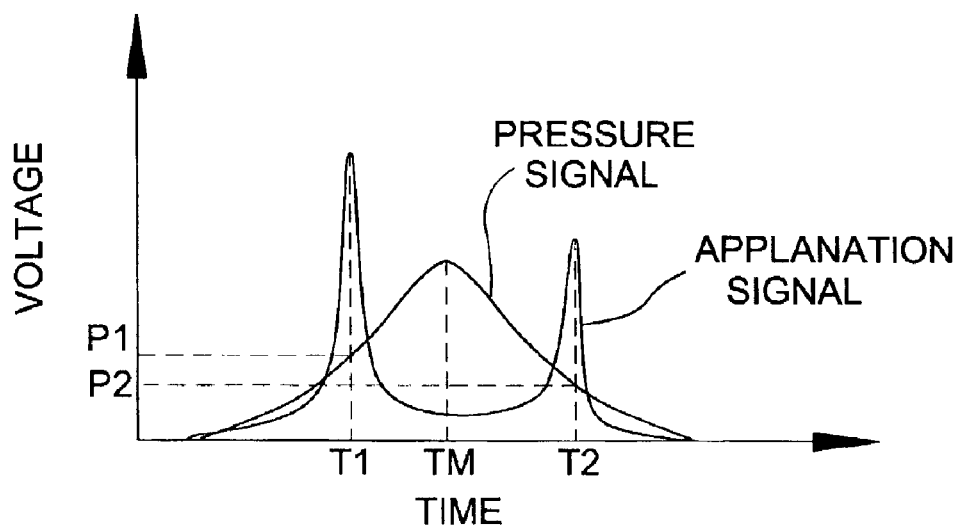
FIG. 6 is a graph of a plenum pressure signal versus time and an applanation detection signal versus time for a typical measurement stoke under the second operational mode.

In accordance with the present invention, NCT 10 is further provided with an alternate measurement mode that is primarily useful in situations where measurements taken in the standard measurement mode, and/or some other observable factor, indicate a possibility of abnormally high or low IOP, and the operator wishes to confirm whether the reading (s) obtained through the standard measurement mode are indicative of true IOP or include significant error due to corneal rigidity effects. FIG. 5 shows drive current as a function of time according to the alternate measurement mode of the preferred embodiment. As can be seen, the solenoid drive current increases linearly for a period of time longer than is necessary to achieve "inward" applanation represented by the first (left hand) peak in the applanation signal before it reverses slope and decreases at the same rate. FIG. 6 shows the resulting pressure-time curve, which is symmetrical about the instant the current reverses slope. As a result, the cornea is transfigured beyond the initial state of applanation to a state of concavity, and then returns through a second "outward" state of applanation to its original state of convexity as the plenum pressure decreases to zero. The outward applanation is represented by the second (right hand) peak in the applanation signal shown in FIG. 6.

As will be observed from FIG. 6, the time T1 of inward applanation and the time T2 of outward applanation are not equidistant from a time TM when the pressure signal reaches a maximum, and the pressure P2 associated with the outward applanation event is less than the pressure P1 associated with the first applanation event. Applicant has experimentally confirmed that this observed hysteresis pressure differential is a rate dependent effect related to the velocity of the fluid pulse, and is not dependent upon IOP. More specifically, applicant has demonstrated that as the pressure ramp is slowed down, the hysteresis decreases in a corresponding manner. Thus, the hysteresis can be thought of as a manifestation of visco-elastic losses in the dynamic system that appear when the rate of the pressure ramp is sufficiently fast and are dependent on physical properties of the cornea, as opposed to IOP.

In the preferred embodiment described herein, the hysteresis is quantified by correlating the first plenum pressure P1 to an IOP in millimeters mercury (IOP1) in the manner known and followed under the standard measurement mode, likewise correlating the second plenum pressure P2 to an IOP in millimeters mercury (IOP2 ), and calculating the hysteresis H by finding the difference:

$$H=IOP1-IOP2.$$

Each tonometric measurement made under the alternate measurement mode is a two-dimensional measurement, wherein the first dimension is simply an IOP value (referred to below as IOPM) based on pressure P1 associated with inward applanation, and the second dimension is hysteresis H. Thus, each alternate mode measurement is a data point comprising a first dimension datum dependent on the force necessary to applanate the cornea and a second dimension datum dependent on physical properties of the cornea itself.

As mentioned above, the alternate measurement mode is concerned with accounting for corneal rigidity effects to provide a measurement that gives the ophthalmic practitioner improved information regarding whether the patient's true IOP is abnormally high or low. The patient's measured IOP can be expressed as follows:

$$IOPM=IOPC+IOPI$$

where IOPM is measured IOP, IOPC is an equivalent IOP offset caused by corneal effects, and IOPI is the true internal ocular pressure that is of diagnostic importance. Following the observations mentioned above with regard to hysteresis H, it is assumed that IOPC is some function of hysteresis H. Thus, $$IOPC=f1(H)$$

By definition, $$IOPI=IOPN+EOP$$

where IOPN is a normal (average) internal pressure which is a constant approximately equal to 14.7 mmHg, and EOP is an "excess" (relative to IOPN) ocular pressure. Setting IOPN equal to a constant K1 and substituting:

$$IOPM=f1(H)+K1+EOP$$

By clinically measuring a statistically large population of N subjects in which EOP is approximately zero, the following relation can be written:

$$IOPM_i=f1(H_i)+K1; \ i=1,N$$

The $IOPM_i$ values can now be fitted to an r order polynomial, for example $$IOPM_i \approx \sum_{j=0,r} a_j H_i^j$$

where $a_0=k1$ and the "a" values can be determined by minimizing the least square differences—i.e., curve fitting the $IOPM_i$ versus the $H_i$ values. The quality of the assumption that the data is well fit with the r order polynomial is evaluated by calculating the traditional correlation coefficient between $IOPM_i$ and $$\sum_{j=0,r} a_j H_i^j.$$

Current data yields a correlation of about 0.9. The curve fitting is not limited to a polynomial, and other functions could be used. Even a tabular smoothed data set could be used but the underlying physics would indicate a simple relationship between second dimension data H and first dimension data IOPM.

Figure 7:
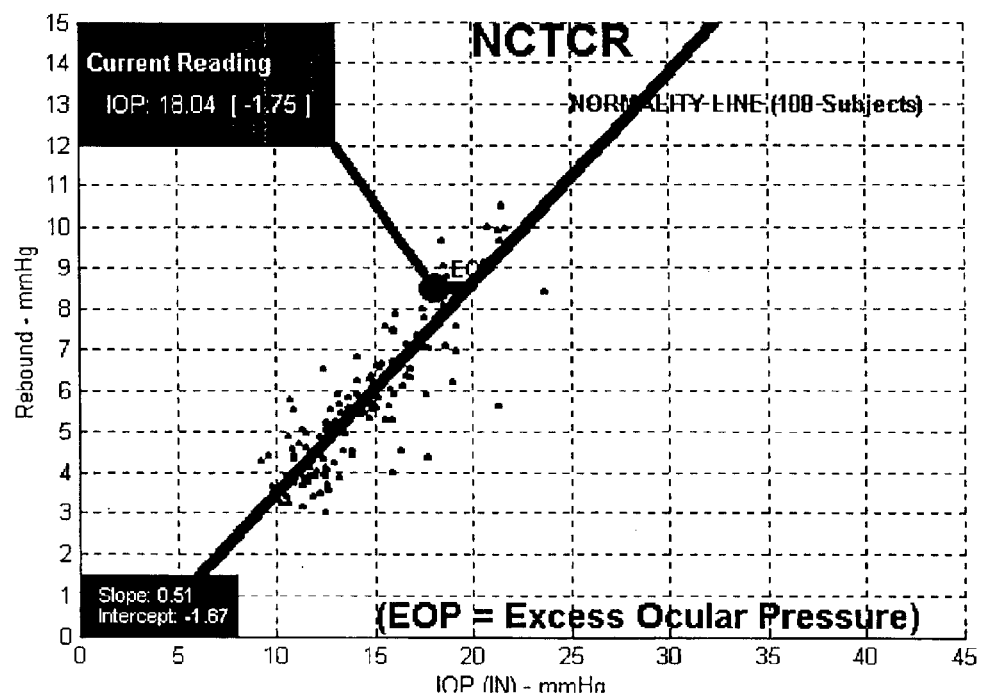
FIG. 7 is a plot showing corneal hysteresis versus measured IOP for a statistical population of eyes, a normality line fitted to the population data points, and a measurement data point taken with respect to a normal right eye of a patient to illustrate comparison of the measured data point to the normality line.
Figure 8:
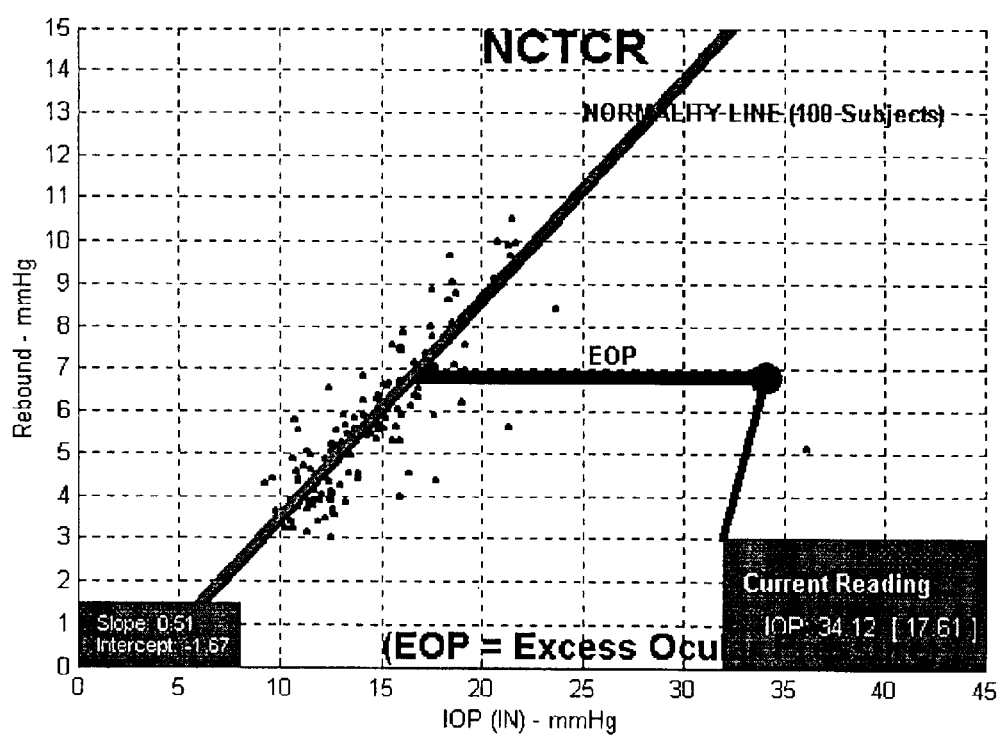
FIG. 8 is a plot similar to that of FIG. 7, however showing a measurement data point taken with respect to a left eye of the patient, wherein the left eye has an artificially elevated IOP to illustrate a high degree of difference from the normality line.

FIG. 7 is a plot of hysteresis H versus IOPM for a statistical population of one-hundred forty-six eyes measured by the same instrument. The plot shows a normality line fitted to the population data points, wherein the line has a slope of 0.51 and a y-intercept of −1.67. This functional relationship is stored in memory 60 as a part of instrument calibration. The plot also shows a two-dimensional measurement data point taken with respect to a patient's right eye wherein IOPM=18.04 mmHg, H≈8.5 mmHg, and EOP=−1.75 mmHg. The population data distribution exhibits an EOP standard deviation of 1.6 mmHg. FIG. 8 is a plot similar to that of FIG. 7 for the left eye of the same patient, however IOP has been artificially elevated by topically administered prednisolone. In FIG. 8, IOPM=34.12 mmHg, H≈6.8 mmHg, and EOP=17.61 mmHg. As can be understood from the foregoing, the alternate measurement mode enables the patient's measured IOP to be compared relative to normality as defined by a predetermined functional relationship stored in memory. The functional relationship can be a line, quadratic function, or other function fitted to the population data set. Under prior art methodology, the patient's measured IOP would simply be compared with a population average measured IOP, with no means of ascertaining whether or to what extent a high reading is due to corneal effects rather than actual elevated IOP. Through the use of hysteresis as a second measurement dimension, error due to corneal effects is essentially eliminated.

What is claimed is:

1. In a non-contact tonometer having a cylinder defining a compression chamber, a piston movable in a forward direction along a stroke axis relative to said cylinder for compressing fluid within said compression chamber, drive means operatively connected to said piston for forcing said piston in said forward direction, energizing means for supplying current to said drive means, a fluid discharge tube in flow communication with said compression chamber for directing a fluid pulse along a test axis, and a pressure sensor arranged to provide a pressure signal associated with said fluid pulse, the improvement comprising:

said energizing means being selectively operable in a plurality of different modes for controlling the pressure versus time behavior of said pressure signal, wherein said drive means comprises a proportional solenoid and wherein said plurality of different modes includes a standard mode wherein said energizing means increases current to said proportional solenoid until said energizing means shuts off current to said proportional solenoid.

2. In a non-contact tonometer having a cylinder defining a compression chamber, a piston movable in a forward direction along a stroke axis relative to said cylinder for compressing fluid within said compression chamber, drive means operatively connected to said piston for forcing said piston in said forward direction, energizing means for supplying current to said drive means, a fluid discharge tube in flow communication with said compression chamber for directing a fluid pulse along a test axis, and a pressure sensor arranged to provide a pressure signal associated with said fluid pulse, the improvement comprising:

said energizing means being selectively operable in a plurality of different modes for controlling the pressure versus time behavior of said pressure signal, wherein said drive means comprises a proportional solenoid and wherein said plurality of different modes includes an alternate mode wherein said energizing means increases current to said proportional solenoid until said pressure signal reaches a peak and then decreases current to said proportional solenoid such that said pressure signal is substantially symmetrical about said peak.

3. A non-contact tonometer comprising:

a fluid pump system including a cylinder, a piston slidably received by said cylinder for axially directed motion relative to said cylinder, and drive means connected to said piston for causing said axially directed motion to compress fluid within a plenum chamber defined by said fluid pump system, wherein said drive means comprises a proportional solenoid;

a fluid discharge tube in flow communication with said fluid pump system to direct a fluid pulse along a test axis to transfigure a cornea of a patient;

applanation detection means for monitoring said cornea and providing an applanation signal indicative of a state of applanation of said cornea caused by said fluid pluse;

a pressure sensor near an inlet end of said fluid discharge tube for providing a pressure signal associated with said fluid pulse;

energizing means for supplying current to said drive means, said enegizing means being selectively operable in a plurality of different modes for controlling the pressure versus time behavior of said pressure signal; and processing means for evaluating said applanation signal and said pressure signal based on a selected one of said plurality of modes to provide a measurement value indicative of intraocular pressure, wherein said plurality of different modes includes a standard mode wherein said energizing means increases current to said proportional solenoid until said energizing means shuts off current to said proportional solenoid, and an alternate mode wherein said energizing means increases current to said proportional solenoid until said pressure signal reaches a peak and then decreases current to said proportional solenoid such that said pressure signal is substantially symmetrical about said peak.

4. The non-contact tonometer according to claim 3, wherein said measurement value is determined in said standard mode by correlating ail amplitude of said pressure signal at a moment said cornea reaches applanation with intraocular pressure.

5. The non-contact tonometer according to claim 3, wherein said measurement value is determined in said alternate mode by evaluating a primary pressure datum corresponding to an inward applanation of said cornea and a hysteresis datum corresponding to a difference between pressure data associated with an inward applanation of said cornea and an outward applanation of said cornea.

6. The non-contact tonometer according to claim 5, wherein said primary pressure datum and said hysteresis datum are evaluated with respect to a predetermined normal functional relationship between primary pressure and hysteresis data for a statistical population of eyes to determine a degree of difference of said measured primary pressure datum from normality.

7. A non-contact tonometer comprising:

a fluid pump system including a cylinder, a piston slidably received by said cylinder for axially directed motion relative to said cylinder, a proportional solenoid connected to said piston to cause said axially directed motion to compress fluid within a plenum chamber defined by said fluid pump system;

a fluid discharge tube in flow communication with said fluid pump system to direct a fluid pulse along a test axis to transfigure a cornea of a patient;

applanation detection means for monitoring said cornea and providing an applanation signal indicative of a state of applanation of said cornea caused by said fluid pulse;

a pressure sensor near an inlet end of said fluid discharge tube for providing a plenum pressure signal associated with said fluid pulse;

energizing means for supplying current to said proportional solenoid, said energizing means being operable to provide a current that increases continuously with time and subsequently decreases continuously with time;

processing means for evaluating said applanation signal and said pressure signal to provide a measurement value indicative of intraocular pressure.

8. The non-contact tonometer according claim 7, wherein said current increases with time and subsequently decreases with time in a symmetrical form about a moment in time.

* * * * *